United States Patent
Finch et al.

[19]

[11] Patent Number: 5,989,239

[45] Date of Patent: Nov. 23, 1999

[54] METHOD AND APPARATUS FOR PERCUTANEOUSLY ACCESSING AN IMPLANTED PORT

[75] Inventors: C. David Finch, Clinton, Miss.; Jeffrey H. Burbank, Boxford; James M. Brugger, Newburyport, both of Mass.

[73] Assignee: VascA, Inc., Tewksbury, Mass.

[21] Appl. No.: 08/896,592

[22] Filed: Jul. 18, 1997

Related U.S. Application Data

[63] Continuation-in-part of application No. 08/856,641, May 15, 1997
[60] Provisional application No. 60/036,124, Jan. 21, 1997.

[51] Int. Cl.⁶ .................................................. A61M 31/00
[52] U.S. Cl. ........................... 604/502; 604/507; 604/93; 604/264
[58] Field of Search .................................. 604/264, 167, 604/175, 93, 49; 206/263–265

[56] References Cited

U.S. PATENT DOCUMENTS

| | | |
|---|---|---|
| 4,181,132 | 1/1980 | Parks . |
| 4,534,759 | 8/1985 | Trawöger . |
| 4,569,675 | 2/1986 | Prosl et al. . |
| 4,634,424 | 1/1987 | O'Boyle . |
| 4,743,231 | 5/1988 | Kay et al. . |
| 4,861,341 | 8/1989 | Woodburn ................................ 604/175 |
| 5,041,098 | 8/1991 | Loiterman et al. ...................... 604/175 |
| 5,053,013 | 10/1991 | Ensmiger et al. . |
| 5,057,084 | 10/1991 | Ensmiger et al. . |
| 5,176,653 | 1/1993 | Metais ..................................... 604/167 |
| 5,180,365 | 1/1993 | Ensmiger et al. . |
| 5,226,879 | 7/1993 | Ensmiger et al. . |
| 5,246,109 | 9/1993 | Markle et al. .......................... 206/263 |
| 5,263,930 | 11/1993 | Ensmiger . |
| 5,281,199 | 1/1994 | Ensmiger et al. . |
| 5,282,789 | 2/1994 | Lundy ....................................... 604/55 |
| 5,350,360 | 9/1994 | Ensmiger et al. . |
| 5,417,656 | 5/1995 | Ensmiger et al. . |
| 5,476,451 | 12/1995 | Ensmiger et al. . |
| 5,503,630 | 4/1996 | Ensmiger et al. . |
| 5,520,643 | 5/1996 | Ensmiger et al. . |
| 5,527,277 | 6/1996 | Ensmiger et al. . |
| 5,527,278 | 6/1996 | Ensmiger et al. . |
| 5,562,617 | 10/1996 | Finch, Jr. et al. . |
| 5,637,088 | 6/1997 | Wenner et al. . |
| 5,792,104 | 8/1998 | Speckman et al. ........................ 604/93 |

FOREIGN PATENT DOCUMENTS

| | | |
|---|---|---|
| WO 95/19200 | 7/1995 | WIPO . |
| WO 9611028 | 4/1996 | WIPO . |
| WO 96/31246 | 10/1996 | WIPO . |

OTHER PUBLICATIONS

Krönung, G. "Plastic Deformation of Cimino Fistula by Repeated Puncture" *Dialysis & Transplantation* (1984) 13(10):635–638.

Scribner, B.H., "The Overriding Importance of Vascular Access" *Dialysis & Transplantation* (1984) 13(10):625.

Scribner, B.H., "Circulatory Access—Still a Major Concern" *Proc. Europ. Dial. Transplant. Assoc.* (1982) 19:95.

Twardowski, Z.J. "Constant Site (Buttonhole) Method of Needle Insertion for Hemodialysis" *Dialysis & Transplantation* (1995) 24(10):559–576.

(List continued on next page.)

*Primary Examiner*—Wynn Wood Coggins
*Assistant Examiner*—Deborah Blyveis
*Attorney, Agent, or Firm*—Townsend and Townsend and Crew LLP

[57] ABSTRACT

Methods and apparatus for percutaneously accessing an implanted port use a large bore coring needle. The coring needle is periodically introduced to an aperture on the implanted port so that the needle passes through the same tissue tract. It has been found that repeated passage of the needle through the same tissue tract reduces patient trauma, with minimized bleeding, reduction in sensitivity, in contrast to the use of non-coring needles.

9 Claims, 5 Drawing Sheets

OTHER PUBLICATIONS

Twardowski, Z.J. "Constant Site Constant Site (Buttonhole) Method of Needle Insertion for Hemodialysis" from Internet Website URL http://aakp.org/btnhol.html printed Oct. 19, 1998, 5 pages total.

Twardowski, Z.J. "Different Sites Versus Constant Sites of Needle Insertion into Arteriovenous Fistulas for Treatment by Repeated Dialysis" *Dialysis & Transplantation* (1979) 8(10):978, 980.

Twardowski et al., "Six–year clinical experiences with the creation and use of internal arteriovenous fistulae in patients treated by repeated haemodialyses (translated)" *Pol. Arch. Med. Wewn.* (1977) 57:205–214. An English abstract is included on p. 213 of this publication.

METHOD AND APPARATUS FOR PERCUTANEOUSLY ACCESSING AN IMPLANTED PORT

The present invention is a continuation-in-part of provisional Application Serial No. 60/036,124, filed on Jan. 21, 1997, and of application Ser. No. 08/856,641 (Attorney Docket No. 17742-001700), filed on May 15, 1997.

BACKGROUND OF THE INVENTION

1. Field of the Invention

The present invention relates generally to the design and use of medical devices. More particularly, the present invention relates to a method and apparatus for accessing an implanted port.

Access to a patient's vascular system can be established by a variety of temporary and permanently implanted devices. Most simply, temporary access can be provided by the direct percutaneous introduction of a needle through the patient's skin and into a blood vessel. While such a direct approach is relatively simple and suitable for applications, such as intravenous feeding, intravenous drug delivery, and other applications which are limited in time, they are not suitable for hemodialysis and other extracorporeal procedures that must be repeated periodically, often for the lifetime of the patient.

For long-term vascular access suitable for hemodialysis, hemofiltration, and the like, the most common approach is to create a subcutaneous arteriovenous (A-V) fistula. The fistula is preferably created by anastomosing an artery, usually the radial artery, to a vein, usually the cephalic vein. The vein dilates and eventually arterializes, becoming suitable for repeated puncture using a needle for access. A-V fistulas may also be created using autologous or heterologous veins, by implanting synthetic blood vessels, typically PTFE tubes, and the like.

The needles used for percutaneously accessing an A-V fistula are large bore coring needles, often referred to as fistula needles. The needles have a bore diameter of 1.49 mm or larger, and permit the high blood flow rates needed for hemodialysis, hemofiltration, and other extracorporeal procedures. One technique for repeatedly accessing an A-V fistula is referred to as the "button hole" technique. Such technique relies on repeatedly accessing the fistula through the same tissue tract, eventually creating a non-healing channel through the tissue overlying the fistula. The channel is lined with scar tissue which forms over time. While generally successful, the button hole technique results in significant bleeding everytime the fistula needle is removed after a treatment is completed. The bleeding, in turn, causes scabbing, and the scab must be removed prior to subsequent needle insertion in order to avoid the risk of pushing scab into the fistula. The removal of the scab causes patient discomfort and bleeding and increases the risk of infection.

As an alternative to the use of an A-V fistula, a variety of implantable ports have been proposed over the years for use in hemodialysis, hemofiltration, and other extracorporeal treatments. Typically, the port includes a chamber having an access region, such as a septum, where the chamber is attached to an implanted cannula which in turn is secured to a blood vessel. In the case of veins, the cannula is typically indwelling, and in the case of arteries, the cannula may be attached by conventional surgical technique.

Percutaneous access to a port through a septum, however, is generally limited to small diameter, non-coring needles. Large diameter needles will core the septum, i.e. form permanent channels therethrough, which will destroy the septum after repeated uses. Small diameter, non-coring needles will remove little or no material from the septum, allowing it to close after the needle is removed. While small needles will thus preserve the septum, they are generally incompatible with the high flow rates which are used with hemodialysis and other extracorporeal treatments.

Implantable ports having an access aperture and internal valve mechanism for isolating the implanted cannula have also been proposed. One type of implantable valved port is described in a series of issued of U.S. patents which name William Ensminger as inventor. The Ensminger access ports have internal lumens for receiving a percutaneously introduced needle and an internal valve structure for isolating the port from an associated implanted cannula. Generally, the Ensminger ports have a needle-receiving aperture which is oriented at an inclined angle relative to the patient's skin. The Ensminger patents do not describe port access using large diameter, coring needles, such as fistula needles. Moreover, as many of the specific Ensminger designs employ elastomeric valve elements, it is likely that the valve mechanisms would be damaged if the ports were accessed by a fistula needle or other large bore coring needle. Representative Ensminger patents are listed in the Description of the Background Art below.

For these reasons, it would be desirable to provide improved methods and apparatus for percutaneously accessing subcutaneously implanted ports. Such methods should reduce patient trauma, provide for reliable access to the implanted port, minimize the risk of infection to the patient, and preferably require only minor modifications to present port implantation procedures. In particular, it would be desirable to provide methods and apparatus for establishing high volume access to subcutaneously implanted ports having valve mechanisms, using large diameter needles, such as conventional fistula needles. Such percutaneous access should accommodate repeated needle penetrations through the same tissue location overlying an aperture of the access port. At least some of these objectives will be met by the invention described hereinafter.

2. Description of the Background Art

U.S. Pat. No. 5,562,617 and WO 95/19200, assigned to the assignee of the present application, describe implantable vascular access systems comprising an access port having an internal slit or duck bill valve for preventing back flow into the port. Vascular access ports having various articulating valves for isolating the port from the vascular system in the absence of external percutaneous connection to the port are described in the following U.S. patents which name William Ensminger as an inventor: 5,527,278; 5,527,277; 5,520,643; 5,503,630; 5,476,451; 5,417,656; 5,350,360; 5,281,199; 5,263,930; 5,226,879; 5,180,365; 5,057,084; and 5,053,013. Other patents and published applications which show implantable ports having valve structures opened by insertion of a needle include U.S. Pat. Nos. 4,569,675; 4,534,759; 4,181,132 and WO 96/31246.

SUMMARY OF THE INVENTION

The present invention provides improved methods, apparatus, and kits for establishing access to subcutaneously implanted ports for a variety of purposes, including hemodialysis, hemofiltration, hemodiafiltration, apheresis, peritoneal dialysis, drug delivery, and the like. The methods rely at least partly on the surprising discovery that repeated percutaneous penetrations with an access needle, even a large bore diameter coring needle, to a subcutaneously implanted, valved access port result in a tissue tract which has minimum bleeding after the needle is removed, which rapidly heals even when accessed multiple times in a single day, and which minimizes patient trauma as the tissue tract loses its nerve sensitivity over time. The tissue tracts which result from accessing such implanted ports differ substantially from those which result from accessing an A-V fistula using the so-called "button hole" technique, even when using identical fistula needles. In particular, the tissue tracts of the present invention do not result in the tunnel ("button hole") which is developed over time with fistula access. It is believed that this difference results at least partly from the ability of the valved port to inhibit bleeding back into the tissue tract when the needle is withdrawn. Inhibition of back bleeding lessens or eliminates scab formation over the penetration point. As discussed above, elimination of the scab obviates the need to remove the scab before the next needle penetration which may occur as soon as several hours later. The ability to eliminate or lessen scab removal is a significant benefit to the patient. In addition, by utilizing the preferred access ports of the present invention, the tissue tract may be formed vertically, thus lessening its length and further reducing bleeding and patient trauma. The access port is also particularly easy to locate beneath the skin, and when combined with the ability to vertically introduce the needle, targeting of the port is greatly simplified. The ability to accurately and simply target the port lessens the chance that the needle will be misdirected, still further reducing patient trauma and enhancing the unique tissue tract formation which underlies the present invention.

According to the present invention, a method for percutaneously accessing an implanted port in a patient comprises providing a needle, typically a coring needle having a bore size of at least 1.16 mm (16 G), preferably being at least 1.33 mm (15 G), more preferably being at least 1.55 mm (14 G), even more preferably being at least 1.73 mm (13 G), and still more preferably being at least 2.08 mm (12 G). The needle is aligned with an aperture on the port, where the port is subcutaneously connected to a blood vessel and the port comprises a valve which selectively isolates the port from the blood vessel. In preferred aspects, the needle is introduced vertically and the valve will open upon insertion of the coring needle into the aperture and will close upon withdrawal of the needle from the aperture. After alignment, the coring needle is percutaneously introduced through tissue overlying the port and into the aperture. The needle will open a blood flow path between the blood vessel and the port.

In another preferred aspect of the method of the present invention, blood is flowed between the blood vessel and a catheter attached to the needle through the port. The needle is then withdrawn from the aperture on the port, and the valve closes to inhibit bleeding from the blood vessel to the tissue tract which was created by the needle. It is still further preferred to subsequently provide another needle, preferably a coring needle having a bore size of at least 1.16 mm. The other needle is then aligned with the aperture on the port and percutaneously (preferably vertically) introduced to the port through the same (at least partially healed) tissue tract which was created by the earlier needle penetration(s). Blood is then flowed between the blood vessel and the catheter (via the port, connecting cannula, etc.) attached to the other needle through the port, and the other needle subsequently withdrawn from the port.

Such repeated needle penetrations will be performed periodically, typically at intervals as short as two hours to as long as four days, usually from four hours to two days. Usually, the coring needle will be introduced in a direction which is generally normal or perpendicular to the skin surface through which it is being introduced, with the repeated access steps eventually creating the nerve depleted tissue tract described above.

The present invention still further provides kits comprising a coring needle having a bore size of at least about 1.16 mm (16 G), such as a fistula needle. The kit further comprises instructions for use setting forth any of the methods described above. The needle and the instructions for use are packaged together, where the instructions may be on a separate instruction sheet and/or may be provided on a portion of the packaging. Usually, the coring needle will be part of a catheter, where the needle is connected or connectable to the catheter to provide a flow path through the needle and into a lumen of the catheter.

DESCRIPTION OF THE SPECIFIC EMBODIMENTS

The methods and apparatus of the present invention for creating a percutaneous access tract are useful with virtually any type of implantable access port having an aperture capable of receiving a needle, preferably a large bore coring access needle. It is further preferred to utilize the methods of the present invention with implantable ports having one, two, three, or more, discrete access ports which may be vertically aligned with the access tract to be percutaneously formed through overlying tissue. Such access tracts will be useful for repeated access to the aperture, where the aperture defines a specific target site through the overlying tissue.

The preferred access ports will have at least one aperture which removably receives the access needle, preferably in a vertical orientation in order to minimize distance of the tissue tract. The access port will preferably be capable of immobilizing the access needle while the blood is being transferred through the port. Exemplary access ports are described in co-pending application Ser. No. 60/036,124, which has previously been incorporated herein by reference. Typically, the port will be implanted beneath the skin by a distance in the range from about 3 mm to 20 mm, usually from 5 mm to 15 mm.

Preferably, the present invention utilizes large bore coring needles, such as conventional fistula needles. By "coring needles," it is meant that the distal tip of the needle will be sharpened and will be open in a forwardly direction so that the needle is capable of cutting tissue (and coring septums) as it is advanced therethrough in a forwardly direction. Less preferred for use in the present invention are needles having a non-coring design, such as Huber needles which have a side-facing distal opening as well as stylets, etc. The preferred needles will have a bore size of at least 1.16 mm (16 G), usually at least 1.33 mm (15 G), more usually at least 1.55 mm (14 G), still more usually at least 1.73 mm (13 G), and sometimes as large as 2.08 mm (12 G), or larger. The needles may be composed of any conventional needle material, typically being a stainless steel, but could also be hard plastic.

Figure 1:
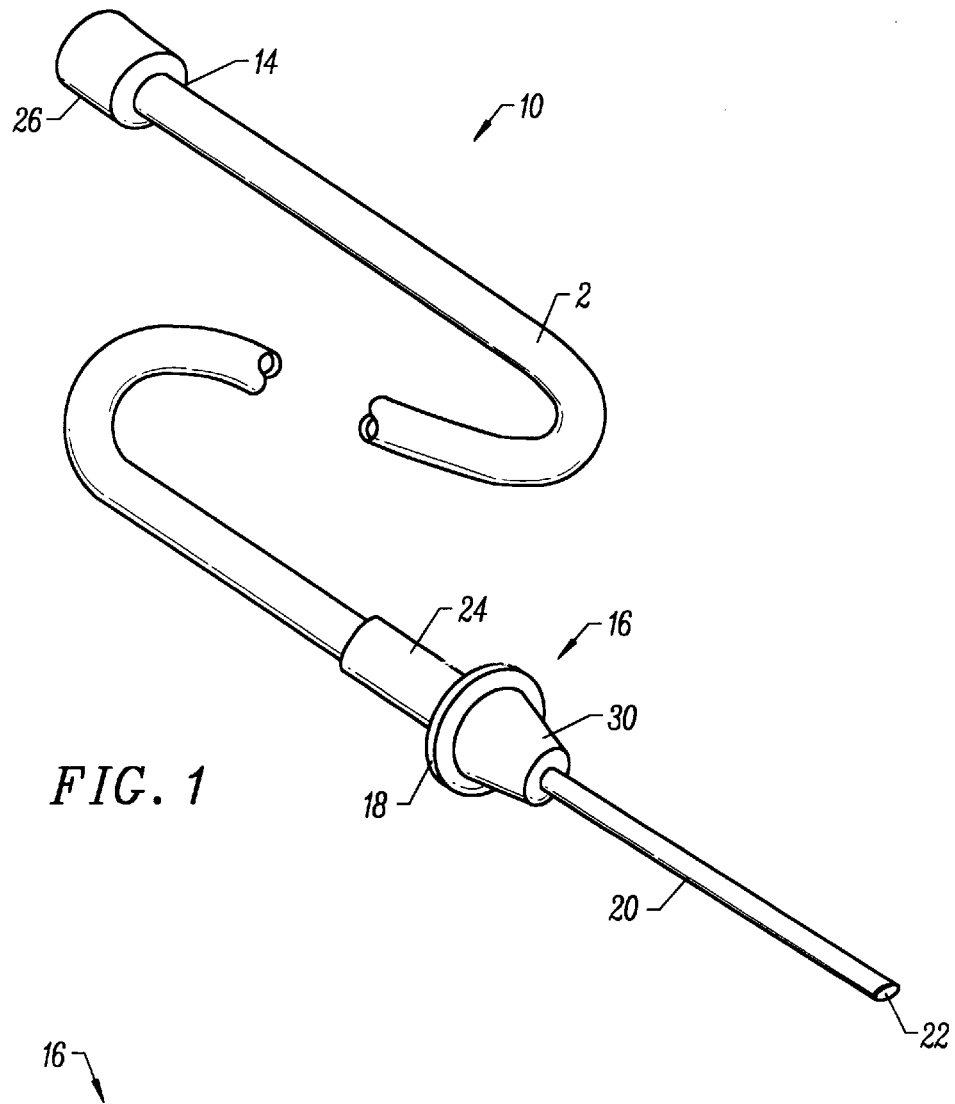
FIG. 1 is a perspective view of a first embodiment of an access catheter having a large diameter coring needle suitable for use in the methods and kits of the present invention.
Figure 2:
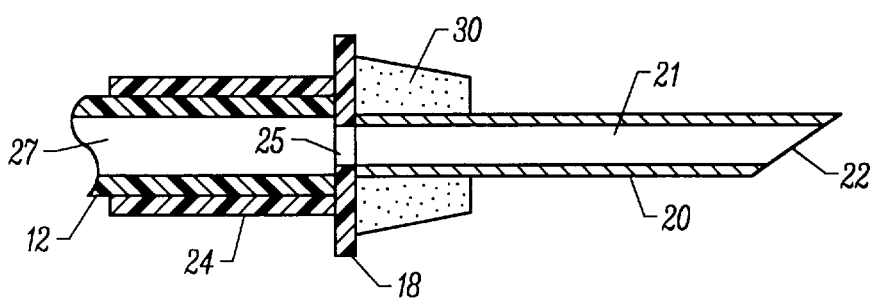
FIG. 2 is a detailed view of the distal end of the catheter of FIG. 1, showing the access needle in cross-section.

Referring now to FIGS. 1 and 2, an access catheter 10 incorporating a large bore coring needle 20 in accordance with the principles of the present invention will be described. The catheter 10 comprises a catheter body 12 having a proximal end 14 and a distal end 16. The catheter body 12 will typically comprise a flexible polymer tube, composed of a medically compatible organic polymer, such as polyvinylchloride, and having a length in the range from 10 cm to 30 cm, preferably from 12 cm to 18 cm, and a lumenal diameter in the range from 1 mm to 5 mm, usually from 3.4 mm to 4.6 mm. Such polymeric tubes may be formed by extrusion and will typically include a single lumen extending the entire length from the proximal end 14 to the distal end 16.

Fitting 18 is secured to the distal end of catheter body 12, typically by an adhesive, heat welding, solvent bonding, penetrating fasteners (not shown), or other conventional means. The fitting is shown as a generally flat disk but could have a variety of alternative geometries. The access tube 20 is secured to the distally forward face of the disk, and the lumen of the needle is fluidly coupled to and aligned with the lumen of catheter body 12. An orifice 25 is disposed in the disk 18 and generally aligned between the lumen 21 of the needle, thus opening into lumen 27 in the catheter body. Usually, a connector 26, such as a luer connector, is provided at the proximal end 14 of the catheter body 12. Such a connector, however, is not necessary and it is possible to directly connect the catheter body to a desired treatment device, fluid source, or other external apparatus.

As described in detail in co-pending Application, a compressible element 30 is attached at the distal end 16 of the catheter body 12. Preferably, the compressible element is coaxially disposed about the proximal end of needle 20. The compressible element 30 may be impregnated with an antiseptic, antibiotic, or other active agent, which can be delivered to the skin's surface as the needle 20 is penetrated therethrough. Such a compressible element, although generally preferred for use in combination with the needles of the present invention, does not form part of the present invention.

Figure 3:
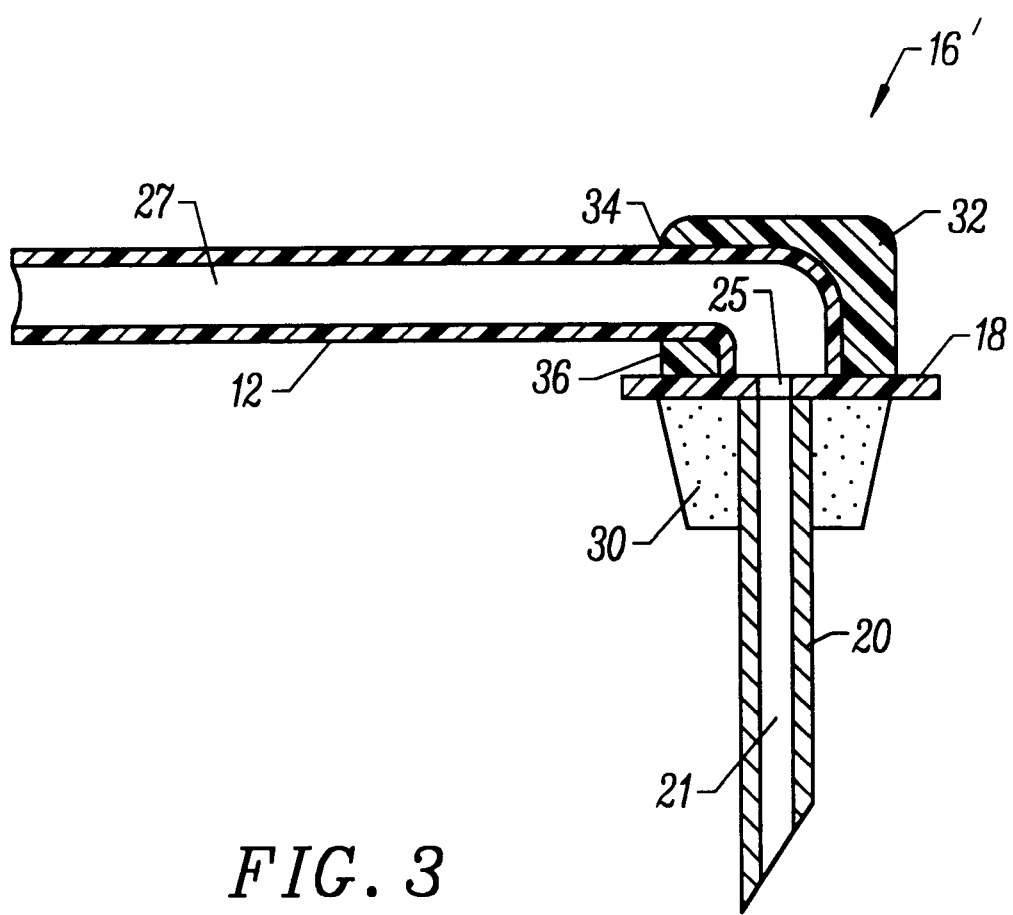
FIG. 3 is a detailed view of an alternative distal end of the catheter of FIG. 1, showing the access needle in cross-section.

Referring now to FIG. 3, an alternative configuration 16' of the distal end of the catheter 10 orients the access needle 20 at an approximately right angle (90°) relative to the distal end of the catheter body 12. The fitting 18 includes cap 32 which defines the 90° bend with an inlet 34 receiving the distal end of the catheter body 12 and an outlet 36 connected to the fitting 18. The catheter body 12 can extend through the internal passage of cap 32 or, alternatively, may be secured at the inlet end. In either case, the substantially continuous lumen 27 is created through the catheter body to the orifice 25 and fitting 18 and thus to the lumen 21 of access needle 20.

Figure 4A:
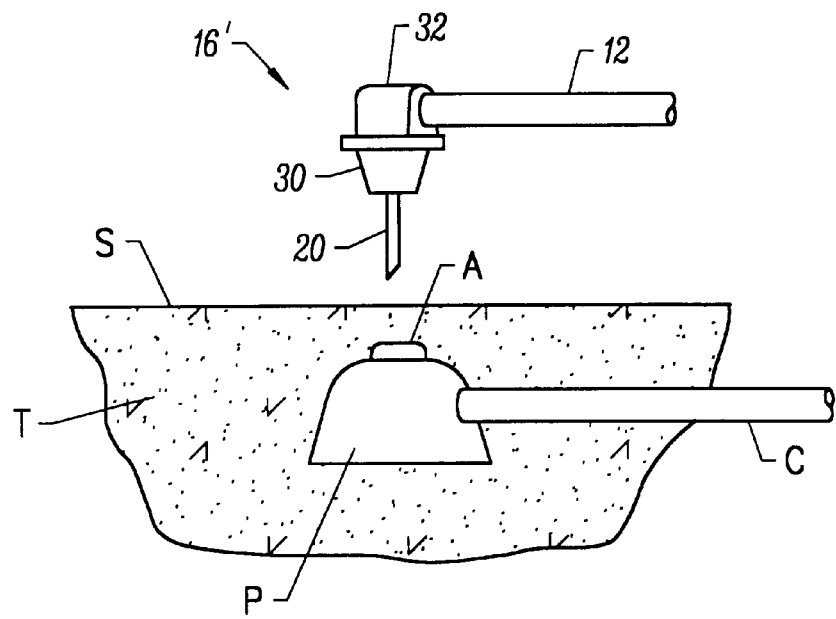
FIGS. 4A–4D illustrate use of the access needle and catheter of FIGS. 1–3 for accessing a subcutaneously implanted port according to the method of the present invention.
Figure 4B:
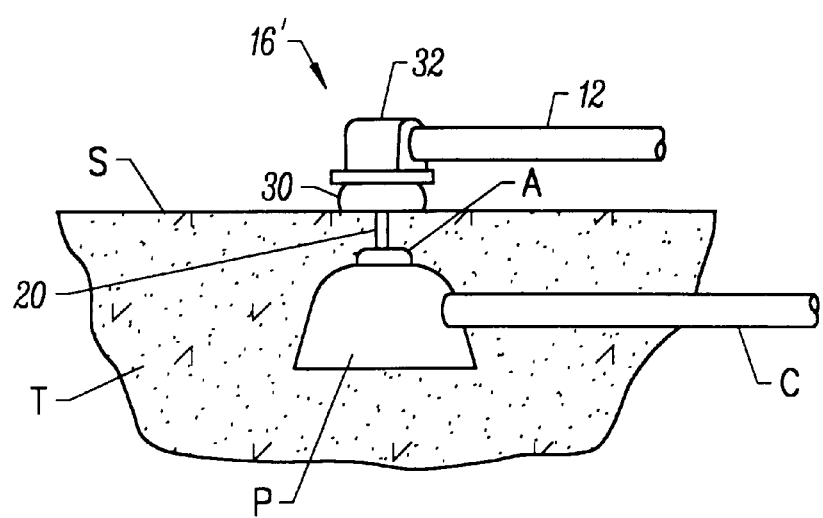

Referring now to FIGS. 4A–4D, use of the catheter 10 having the distal end 16' (FIG. 3) and access needle 20 for accessing an implanted port P will be described. The port P will have an aperture A which is preferably oriented to receive a vertically aligned needle. That is, the access needle 20 will preferably be percutaneously introduced through the skin surface S in a direction which is normal to or perpendicular to the plane of the skin at the point where the needle is being introduced. After entering the port P, the access needle 20 will actuate an internal valve (not shown) to open a flow path with a lumen and cannula C, where the cannula may be connected to a blood vessel or other body lumen or cavity, as described in detail in co-pending Application. The access needle 20 may be aligned over the aperture A by manually feeling the top of the port P. The port P is generally symmetric with the aperture positioned in the center of the port. The user can feel the periphery of the port P and visually determine its center. The needle 20 is then vertically penetrated through the skin and into the aperture, as shown in FIG. 4B. The thickness of tissue T overlying the aperture is generally from 3 mm to 15 mm, as described above.

Figure 4C:
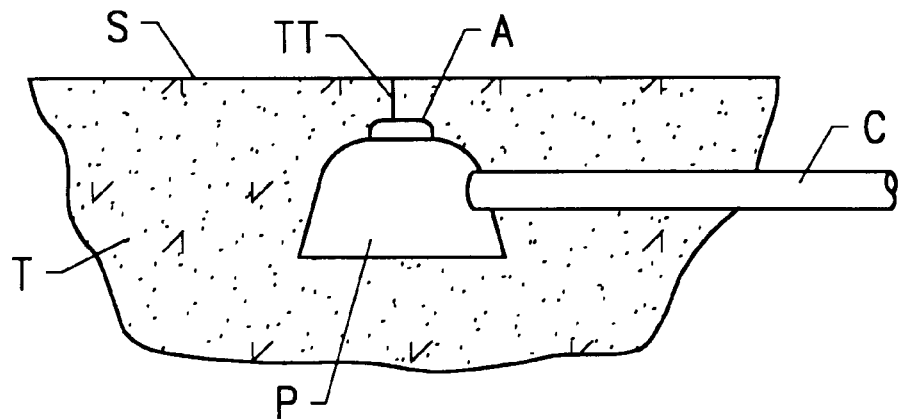

The needle 20 will be left in place in port P while the desired procedure, such as hemodialysis, hemofiltration, peritoneal dialysis, or other procedure, is performed and completed. After completion of the procedure, the needle 20 will be withdrawn, as illustrated in FIG. 4C. Withdrawal of the needle will leave a tissue tract TT through the tissue T overlying the port P. Because the internal valve of port P will have closed, bleeding from the body lumen, typically a blood vessel, will be inhibited. Both the vertical orientation of needle entry and the inhibition of back bleeding into the tissue tract which is left after withdrawal of the needle contribute to the lessening or elimination of scab formation and reduction in patient trauma and rapid healing in a non-fibrous manner. Surprisingly, such benefits may be achieved even when using the preferred large bore access needles described above. The rapid healing and minimum trauma have been found even when the port is accessed as many as four times per day. Such a result could not have been predicted prior to the present invention and provides substantial advantages over the use of the non-coring needles typically used with implanted ports.

Figure 4D:
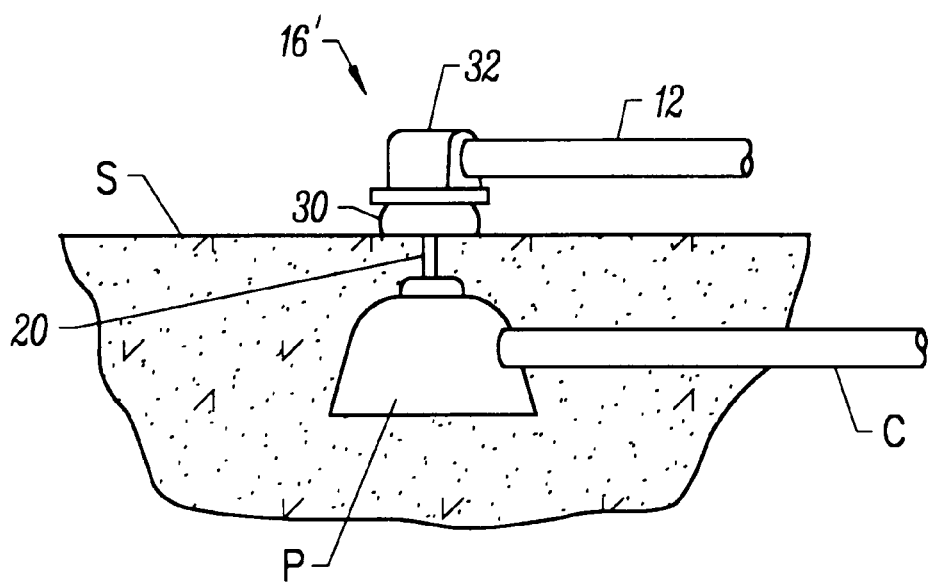

The tissue tract remaining after withdrawal of the catheter, as shown in FIG. 4C, is ready to receive a second catheter as shown in FIG. 4D virtually immediately after the first catheter is withdrawn. Typically, additional access needles 20 and associated catheters will be introduced over periods of from two hours to four days, usually from four hours to two days. Such cycle times are suitable for performing a wide variety of chronic procedures, such as hemodialysis, hemofiltration, peritoneal dialysis, and the like.

Figure 5:
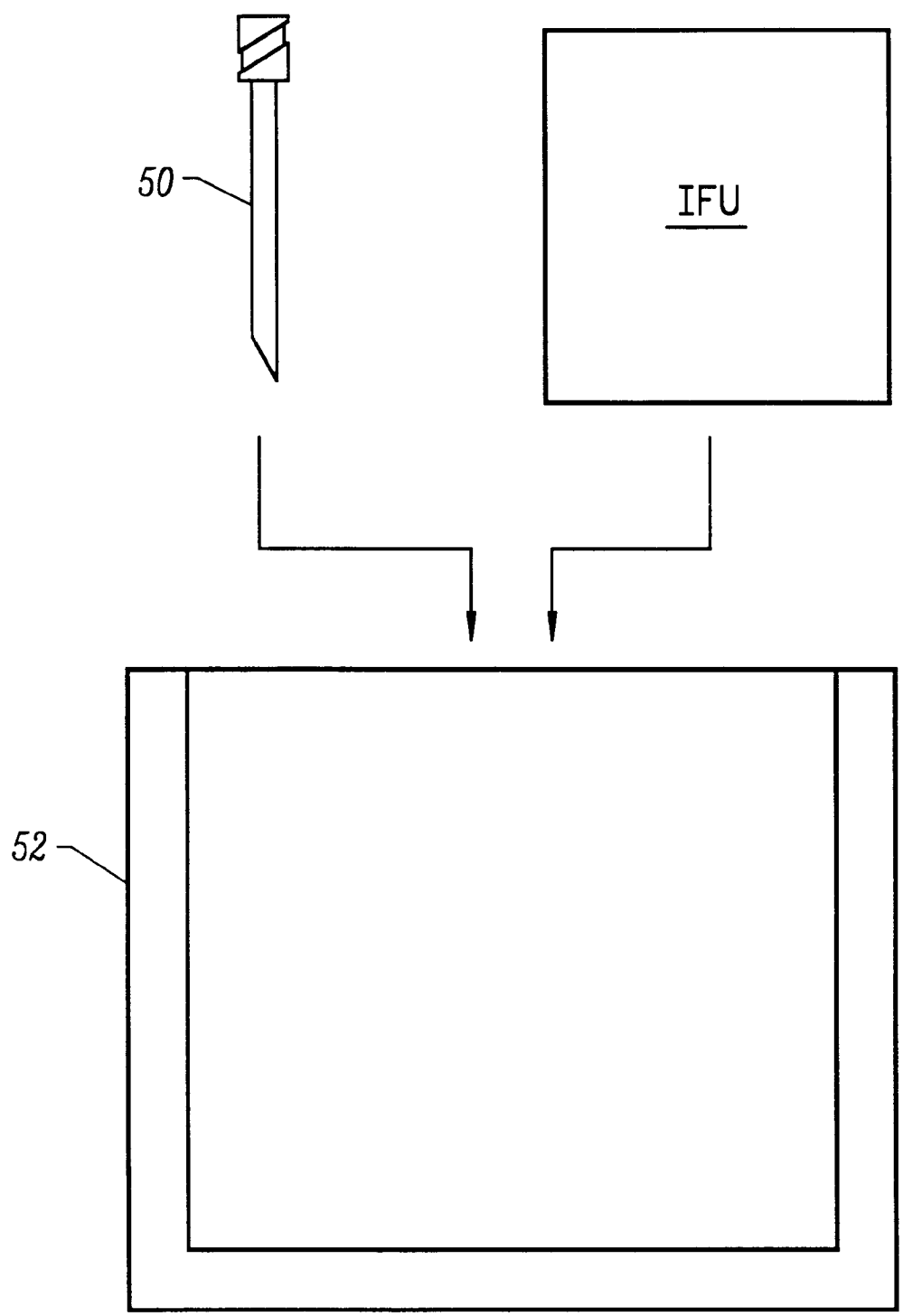
FIG. 5 illustrates a kit according to the present invention comprising a large bore coring needle, a package, and instructions for use.

Referring now to FIG. 5, a needle 50, typically a large bore coring needle, according to the present invention, may be packaged together with instructions for use (IFU) in a kit, as shown in FIG. 5. A conventional package which may be a pouch 52 or any other suitable package, such as a tray, box, tube, or the like, may be used to contain the needle 50 and the IFU, where the IFU may be printed on a separate sheet and/or may be printed on the packaging itself. Optionally, but not necessarily, the needle may be sterilized within the package, e.g. by radiation or ethyleneoxide. The instructions may set forth any of the aspects of the method of the present invention described above.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for percutaneously accessing an implanted port in a patient, said method comprising:
   (a) providing a needle;
   (b) aligning the needle with an aperture on the port, wherein the port is subcutaneously connected to a blood vessel and contains a valve which isolates the aperture from the blood vessel;
   (c) percutaneously introducing the needle through tissue overlying the port and into the aperture, wherein the needle opens a blood flow path between the blood vessel and the port;
   (d) flowing blood between the blood vessel and a catheter attached to the needle through the port; and
   (e) withdrawing the needle from the aperture, wherein the valve closes to inhibit bleeding from the blood vessel to a tissue tract created by the needle;
   (f) providing another needle;
   (g) aligning the other needle with the aperture on the port;
   (h) percutaneously introducing the other needle through the same tissue tract into the aperture, wherein the needle opens a blood flow path between the blood vessel and the port;
   (i) flowing blood between the blood vessel and a catheter attached to the other needle through the port; and
   (j) withdrawing the other needle from the aperture, wherein the valve closes to inhibit bleeding from the blood vessel to a tissue tract created by the needle.

2. A method as in claim 1, wherein the needle has a bore size of at least 1.16 mm.

3. A method as in claim 1, wherein the other needle has a bore size of at least 1.16 mm.

4. A method as in claim 1, wherein the steps (g) through (j) are performed from two hours to four days after step (e).

5. A method as in claim 1, further comprising repeating steps (f) through (j) periodically.

6. A method as in claim 5, wherein the steps (f) through (j) are repeated every two hours to every four days.

7. A method as in claim 1, wherein the needles are introduced in a direction generally normal to the skin surface at the point through which it passes.

8. A kit comprising:
   a needle;
   instructions for use setting forth the method of claim 1; and
   a package containing the port and instructions.

9. A kit as in claim 8, further comprising a catheter connected or connectable to the needle.

* * * * *